United States Patent [19]

Pfeiffer et al.

[11] Patent Number: 5,305,744
[45] Date of Patent: Apr. 26, 1994

[54] CALIBRATING REFLECTOR DEVICE FOR AN OPTICAL MEASURING SYSTEM

[76] Inventors: Ulrich Pfeiffer, Metzstr. 29a, D-8000 Munich; Reinhold Knoll, Kirchenstr. 88, D-8000 Munich 80, both of Fed. Rep. of Germany

[21] Appl. No.: 32,862

[22] Filed: Mar. 17, 1993

[30] Foreign Application Priority Data

Mar. 18, 1992 [DE] Fed. Rep. of Germany ....... 4208707

[51] Int. Cl.⁵ ................................................ A61B 5/00
[52] U.S. Cl. .................................... 128/634; 356/243
[58] Field of Search ............................... 128/633–635, 128/664–667; 356/39–41, 243

[56] References Cited

U.S. PATENT DOCUMENTS

| 4,322,164 | 3/1982 | Shaw et al. | |
|---|---|---|---|
| 4,691,709 | 9/1987 | Cohen | 128/667 |
| 4,796,633 | 1/1989 | Zwirkoski | |
| 4,823,167 | 4/1989 | Manska et al. | 128/634 X |
| 4,981,355 | 1/1991 | Higgins | 128/634 X |
| 4,986,671 | 1/1991 | Sun et al. | 128/666 X |
| 5,179,936 | 1/1993 | O'Hara et al. | 128/664 X |

Primary Examiner—Angela D. Sykes
Attorney, Agent, or Firm—Sixbey, Friedman, Leedom & Ferguson

[57] ABSTRACT

Calibrating reflector device to calibrate an optical measuring system having an optical fiber optics probe, for example, for measuring the oxygen saturation of blood. The calibrating reflector device comprises a housing that is open on one end, a reflecting device in the form of an opaque layer in which reflecting particles are embedded, as well as a positioning plug with a central bore, in which the fiber optics probe can be received with a certain frictional resistance. A transparent layer is disposed between the front end of fiber optics probe and the reflecting layer, on whose surface the front end of fiber optics probe can be arranged by the positioning plug.

20 Claims, 1 Drawing Sheet

CALIBRATING REFLECTOR DEVICE FOR AN OPTICAL MEASURING SYSTEM

BACKGROUND OF THE INVENTION

1. Field of the Invention

The invention relates to a calibrating reflector device for an optical measuring system which has an optical fiber optics probe, with a housing that is open on one side, a reflecting device with a specific reflection behavior and a positioning device, which places the front end of the fiber optics probe in the housing of the reflecting device.

2. Description of Related Art

A calibrating reflector device of the type to which the present invention relates is known from U.S. Pat. No. 4,796,633.

Calibrating reflector devices are used to calibrate optical measuring systems which are used to measure parameters of a sample, which can be detected by spectroscopic differences in the sample. These include, for example, catheter oxygen measuring systems, which are used to measure the oxygen saturation of the blood. To measure the oxygen saturation of the blood in vivo, the fiber optics probe is placed in the circulatory system of the patient.

In such optical measuring systems, the fiber optics probe comprises, for example, a thin tube with two optical waveguides whose measuring-side end is cut off vertically and polished. The light coming from a light source, going through an optical waveguide when measuring, strikes the sample to be measured and is scattered by the sample. The scattered light is recollected and evaluated for measurement. The measurements take place with light of various wavelengths, and, for example, the oxygen saturation of the blood is determined by a ratio formation of the measured values of various wavelengths.

Optical measuring systems of this type have to be calibrated, since the systems age over time and a measured value drift occurs. The reason for this lies, e.g., in such facts as that water accumulates in the plastic of the optical waveguide, that transmission changes occur, that the reproducibility of the connector between the fiber optics probe and the light source to be connected or the evaluating device to be connected changes, or that the light-sending diodes of the light source age.

Without a calibration of the optical measuring system, no absolute measurements can be obtained, only relative values can be measured. A measurement of absolute values requires a readjustment of the optical measuring system to a standard. For this purpose, calibrating reflector devices are used, which represent such a standard and are used before the actual measurement to calibrate the optical measuring system. To calibrate the optical system, the optical fiber optics probe is placed in the calibrating reflector device, which has a specific fixed reflection behavior. Then, the measuring system is calibrated from the results of measurements obtained, for example, by adjusting the obtained measuring signal amplitude on the measuring device. After calibration with a calibrating reflector device, which is used only once, the actual measurements can take place.

Calibrating reflector devices of the usual type of construction can be subdivided into so-called solid-state reflectors and so-called cavity reflectors.

An example of a known cavity reflector is the initially mentioned calibrating reflector device, which is known from U.S. Pat. No. 4,796,633. In this known device, reflecting particles are embedded in the front surface of an inside wall of the housing, and the front end of the fiber optics probe is placed at a predetermined distance opposite this front surface. For calibration, light of specific wavelengths is thrown by the fiber optics probe onto the front surface having the reflecting particles and the light reflected from the surface is absorbed and used for calibration.

However, in such a cavity reflector, the optical properties are influenced by the surface condition of the cavity walls, i.e., the inner walls of the housing, the surface condition of the light exit surface on the front end of the fiber optics probe and the exact positioning of the fiber optics probe in the housing. Since such reflectors are produced as a unit in an injection molding process, the optical properties are, moreover, influenced by the distribution, shape and size of the reflecting particles, which are embedded in the housing wall.

An example of a known solid-state reflector can be found in U.S. Pat. No. 4,322,164. In this solid-state reflector, a solid element is provided inside a housing, in which light-dispersing particles are embedded and cause a clouding, so that this solid-state element has a specific known reflection behavior and forms the measuring standard. To assure a reliable contact between the surface of this solid-state element and the front end of the fiber optics probe, the solid-state element is mounted in the housing to be axially resiliently displaceable, i.e., in the axial direction of the fiber optics probe. Additionally, the opposite side of the solid-state element, relative to the fiber optics probe, is provided with a pretensioning device, for example, in the form of a spring, by which the solid-state element is pressed firmly against the front end of the fiber optics probe during calibration.

However, in such solid-state reflectors, the optical properties of the reflector are influenced by the distribution, shape and size of the reflecting particles in the solid-state element. These parameters can be poorly controlled in the production of the reflector. The reflecting particles on the surface of the solid-state element, because of the spring pretensioning, are in a constant firm contact with the front end of the fiber optics probe, so that the danger exists that the particles detach themselves from the solid-state element. Moreover, it is not possible to easily change the type of particle since, as a rule, a change of the production process is necessary to do so. As a result, the variability of the reflection behavior in such reflectors is small.

In the solid-state reflector described in U.S. Pat. No. 4,322,164, stray reflections, especially on the coupling surface of the front end of the fiber optics probe, which occur, for example, in cavity reflectors can be avoided by the resilient pressing of the solid-state element against the front end of the fiber optics probe; however, the firm contact produced between the probe and solid-state element causes the particle distribution to be at least partially disturbed.

SUMMARY OF THE INVENTION

In view of the foregoing, a principle object of the present invention is to provide a calibrating reflector device of the initially mentioned type which will have greater accuracy due to it being subject to fewer disturbing influences.

This object is achieved according to a preferred embodiment of the invention by providing a calibrating reflector device in which a transparent layer is placed in front of a reflecting device so that the front end of a fiber optics probe is placed adjoining the transparent layer by a positioning device.

In the calibrating reflector device according to the invention, the quality of the calibration is mainly determined by the transparent layer and the reflecting device alone, so that the other components of the device can exert no disturbing influences. Thus, the other components of the calibrating reflector device can be produced according to any process. Because of the transparent intermediate layer, all centers of reflection are approximately at the same distance from the front end of the optical fiber optics probe. As a result, the size, shape and density of the reflecting particles of the reflecting device have a small influence on the quality of the calibration.

Another basic advantage of the design according to the invention is the possibility to control the reflection behavior utilizing the considerable leeway in the selection of the reflecting particles that is available. By matching the index of refraction of the optical waveguides and transparent layer, stray reflections on the light exit surface of the optical fibers can be avoided.

The calibrating reflector device according to the invention, thus, produces highly reproducible results and few disturbances of the optical properties by side effects, such as, for example, stray reflections on the coupling surface of the optical fiber optics probe relative to the reflecting device. Furthermore, calibrating reflector devices can be produced which have consistent characteristics from one to another, so that the calibration produced does not vary significantly from one calibrating reflector device to another.

These and further objects, features and advantages of the present invention will become apparent from the following description when taken in connection with the accompanying drawings which, for purposes of illustration only, a single embodiment in accordance with the present invention.

DETAILED DESCRIPTION OF THE PREFERRED EMBODIMENT

Figure 1:
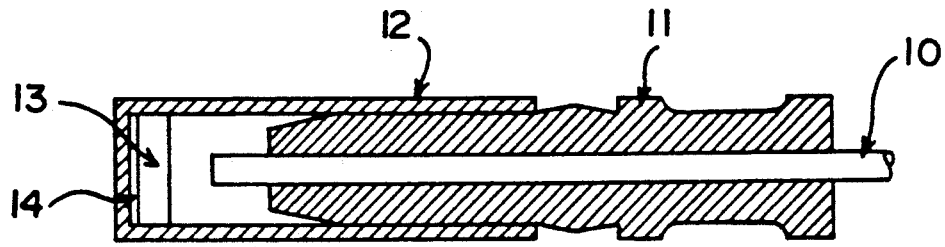
FIG. 1 is a sectional view of a preferred embodiment of the calibrating reflector device according to the invention with a fiber optics probe partially inserted.

The embodiment of the calibrating reflector device according to the invention, represented in the drawing, basically comprises a housing 12, for example, of an opaque plastic, which is elongated and open at one end. A reflecting or opaque disk or layer 14, as well as a transparent layer or disk 13, are provided in the housing 12 with the disk or layer 14 arranged axially inwardly of the transparent disk or layer 13. For simplicity, in the following description and claims, only the term layer is used; but, it is intended that the term layer encompass the use of a disk, sheet, film, coating or the like having the requisite optical characteristics.

Figure 3:
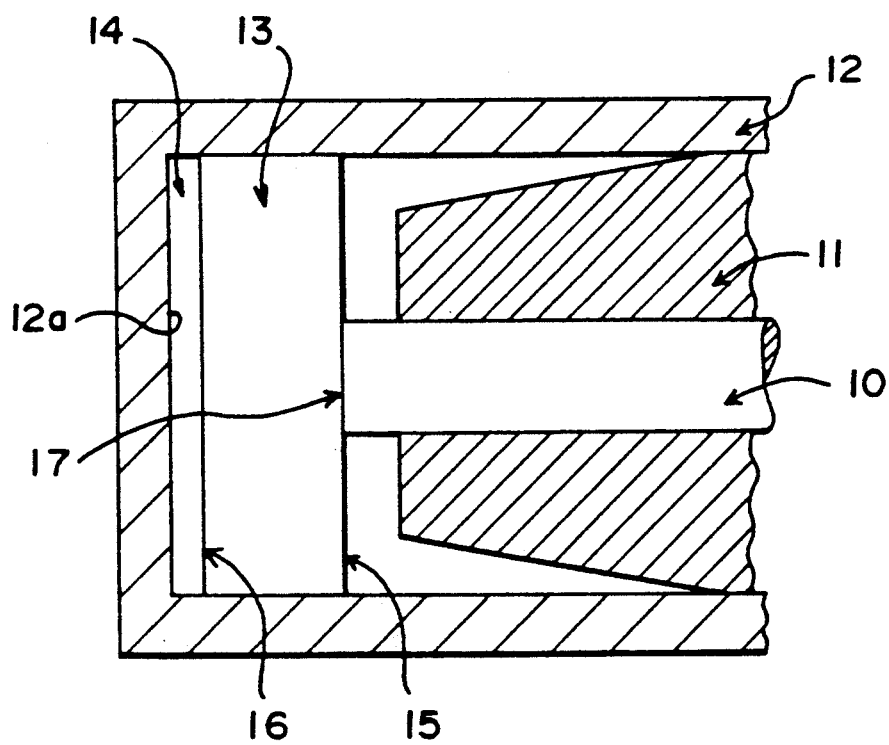
FIG. 3 is an enlarged partial sectional view of the optically active area of the preferred embodiment of the calibrating reflector device according to the invention as shown in FIG. 2.

As it is represented in FIG. 3, the optically active area is comprised of the transparent layer 13 and the opaque layer 14, which are connected firmly with one another without a gap. Transparent layer 13 has a coupling surface 15 on one side and a reflecting surface 16 on an opposite side, i.e., at its interface with opaque layer 14. The contour of coupling surface 15 is matched to that of the end face 17 of the fiber optics probe or measuring probe 10, and usually a flat coupling surface 15 is provided.

Opaque layer 14, which forms the reflecting device, can consist of a coating on the transparent layer 13 or of a thin disk in which synthetic resin bonded pigments are bound. The coating can be applied to transparent layer 13, for example, via a silk-screen printing process. But, opaque layer 14, also, can be formed by suitable pigments being introduced into the front surface 12a of the housing 12, so that this impregnated front surface, itself, constitutes the opaque layer. In this case, transparent layer 13 is placed directly, i.e., without a gap, on the front surface 12a of housing 12.

Transparent layer 13, and optionally opaque layer 14, are preferably pushed loosely into housing 12. The pigment mixture used for forming the reflecting device, i.e., opaque or reflecting layer 14, has a known specific mixing ratio, which can easily be changed to vary the reflection properties.

Transparent layer 13 is transparent, in the ideal case without absorption, and consists, for example, of an elastic, transparent plastic, such as, for example, a silicone.

Reflecting surface 16, according to FIG. 3, can also be formed by a rough, partially reflecting interface, and in this case, opaque layer 14 is replaced by a layer with a lower index of refraction. This can also be an air layer.

Figure 2:
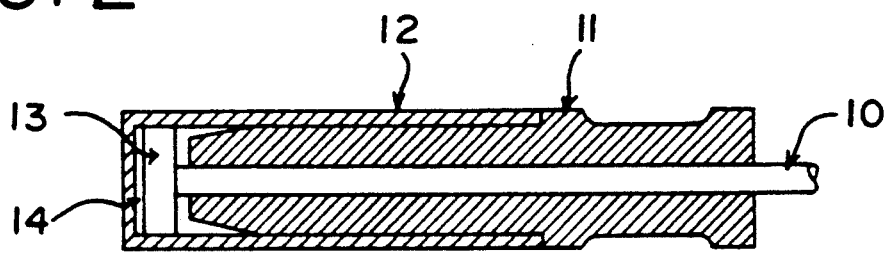
FIG. 2 is a sectional view of the calibrating reflector device according to the invention with the fiber optics probe fully inserted.

A holding plug 11, made of an elastic material, is provided with a central bore for receiving the front end of fiber optics probe 10. The diameter of this bore is configured so that fiber optics probe 10 is received in it with a limited frictional resistance, i.e., sufficient to hold the probe in place but not so high as to make insertion and removal too difficult. Lugs or projections are formed on the plug 11 at an axial distance from its front end that is set so that, when plug 11 is fully inserted into the position shown in FIG. 2, the front end of the fiber optics probe adjoins the surface 15 of transparent layer 13 without a gap therebetween. Layer 13, thus, provides a space between the front end of fiber optics probe 10 and opaque layer 14, i.e., the reflecting device.

For protection from outside light, housing 12 and holding plug 11, preferably, are make of an opaque material.

The above-described embodiment of the calibrating reflector device according to the invention is used in the following way:

The reflector device is applied and tested in the production of the measuring system, i.e., optical fiber optics probe 10 is in an operative state on the optical measuring system. Probe 10 and the reflector device remain connected with one another until use. Directly before the use, the probe with the reflector device thereon is tested by the user as a standard, and the related measuring system is calibrated.

For assembly, fiber optics probe 10 is plugged into holding plug 11. Probe 10 is pushed through holding plug 11 to a certain extent until its end projects from holding plug 11. Then, holding plug 11 with probe 10 therein is inserted into housing 12. Probe 10 is firmly held in the housing 12 by the resilient deformation of holding plug 11. If the front surface of probe 10 comes into contact with coupling surface 15 of transparent layer 13, probe 10 is pushed back into holding plug 11 against the frictional force therebetween. In this way, it is assured that the front end of probe 10 firmly adjoins coupling surface 15 of transparent layer 13.

The static friction between housing 12, holding plug 11 and probe 10 results in a permanent immobilization of probe 10 in its position. By the elastic deformation of holding plug 11, probe 10 also remains on coupling surface 15 after assembly. In connection with the elasticity of transparent layer 13, a reflection-free light coupling is thus achieved.

To calibrate probe 10, light from probe 10 is radiated from its coupling end surface 17 into transparent layer 13. The light strikes reflecting surface 16 and is reflected diffusely and wavelength-selectively by the latter. A part of the reflected light is thrown back into probe 10 and can be evaluated for calibration of the measuring system.

By variation of the thickness of transparent layer 13 and reflecting surface 16 or reflecting layer 14, the optical behavior can be changed.

For conducting actual measurements, after calibration, holding plug 11 is, then, pulled out from housing 12, by which the holding plug 11 returns to its original shape. Measuring probe 10 is, thus, released and can be removed from holding plug 12 and used for the actual measurements.

In the calibrating reflector device according to the invention, the reflection behavior can be controlled, in a simple way, with the same production process by the selection of the reflecting particles used so as to match the index of refraction of the optical waveguides and transparent layer to avoid stray reflections on the light emitting surface of the optical fibers at surface 17 of the probe 10. This can be achieved, for example, by a change in the thickness of transparent layer 13. The spectral behavior can be changed by the pigmentation of opaque layer 14. Transparent layer 13 can be punched from a plate material, and opaque layer 14 can be applied in advance via a silk-screen printing process. This results in reasonably-priced, reproducible production.

The quality of the calibration is mainly determined by transparent layer 13 and opaque layer 14. As a consequence, all other components can be produced according to any processes, since they cannot exert any disturbing influences.

No special requirements on the design of the catheter for use in vitro for measuring oxygen saturation in the blood are imposed by the present invention.

Stray reflections are avoided by the exactly fit coupling, matched to the index of refraction, of the optical fiber optics probe to the reflection standard.

While we have shown and described various embodiments in accordance with the present invention, it is understood that the same is not limited thereto, but is susceptible of numerous changes and modifications as known to those skilled in the art, and we, therefore, do not wish to be limited to the details shown and described herein, but intend to cover all such changes and modifications as are encompassed by the scope of the appended claims.

We claim:

1. Calibrating reflector device, for an optical measuring system which has an optical fiber optics probe, the reflector device comprising a housing that is open at one end, a reflecting device in said housing, said reflecting device having a specific reflection behavior and a positioning device which positions a front end of a fiber optics probe of an optical measuring system in the housing of the reflector device; wherein a transparent layer is placed adjacent the reflecting device in a manner causing the front end of a fiber optics probe to be positioned in the housing, by said positioning device, adjoining the transparent layer.

2. Calibrating reflector device according to claim 1, wherein the reflecting device comprises a reflecting layer which contains reflecting particles.

3. Calibrating reflector device according to claim 2, wherein the reflecting layer is placed on the transparent layer.

4. Calibrating reflector device according to claim 1, wherein the reflecting device comprises a front surface of an inner wall of the housing in which reflecting particles are embedded.

5. Calibrating reflector device according to claim 1, wherein a surface of the transparent layer abuts the reflecting device in a manner creating a rough, partially reflecting interface therebetween; and wherein the reflecting device comprises an opaque layer with a lower index of refraction than said interface.

6. Calibrating reflector device according to claim 1, wherein the positioning device comprises an elastic plug which has a central opening extending axially therethrough for frictionally retaining the fiber optics probe therein.

7. Calibrating reflector device according to claim 6, wherein the reflecting device comprises a reflecting layer which contains reflecting particles.

8. Calibrating reflector device according to claim 7, wherein the reflecting layer is placed on the transparent layer.

9. Calibrating reflector device according to claim 6, wherein the reflecting device comprises a front surface of an inner wall of the housing in which reflecting particles are embedded.

10. Calibrating reflector device according to claim 6, wherein a surface of the transparent layer abuts the reflecting device in a manner creating a rough, partially reflecting interface therebetween; and wherein the reflecting device comprises an opaque layer with a lower index of refraction than said interface.

11. Calibrating reflector device according to claim 6, wherein said elastic plug has limiting means on an outer side thereof for positioning the elastic plug in said housing.

12. Calibrating reflector device according to claim 11, wherein the reflecting device comprises a reflecting layer which contains reflecting particles.

13. Calibrating reflector device according to claim 12, wherein the reflecting layer is placed on the transparent layer.

14. Calibrating reflector device according to claim 11, wherein the reflecting device comprises a front surface of an inner wall of the housing in which reflecting particles are embedded.

15. Calibrating reflector device according to claim 11, wherein a surface of the transparent layer abuts the reflecting device in a manner creating a rough, partially reflecting interface therebetween; and wherein the reflecting device comprises an opaque layer with a lower index of refraction than said interface.

16. Calibrating reflector device according to claim 1, wherein said reflecting layer comprises an opaque disk.

17. Calibrating reflector device according to claim 1, wherein said transparent layer comprises a disk of transparent material.

18. Calibrating reflector device according to claim 17, wherein said reflecting layer comprises an opaque disk in abutting relationship with said disk of transparent material, both of said disks being loosely received in said housing.

19. Calibrating reflector device according to claim 18, wherein said positioning device comprises an elastic plug which has a central opening extending axially therethrough for frictionally retaining the fiber optics probe therein.

20. Calibrating reflector device, for an optical measuring system which has an optical fiber optics probe, the reflector device comprising a housing which is open at one end, a reflecting device in said housing, said reflecting device having a specific reflection behavior and a positioning device which positions a front end of a fiber optics probe of an optical measuring system in the housing of the reflector device; wherein a transparent layer is provided in juxtaposition to the reflecting device in said housing, said transparent layer being disposed between the reflecting device and the open end of the housing and forming an abutment means for properly positioning the front end of a fiber optics probe relative to the reflecting device by engagement of said front end on said transparent layer when the optics probe is positioned in the housing by said positioning device.

* * * * *